Sept. 21, 1948. J. BACH Plant Pat. 807
IVY PLANT
Filed April 19, 1947
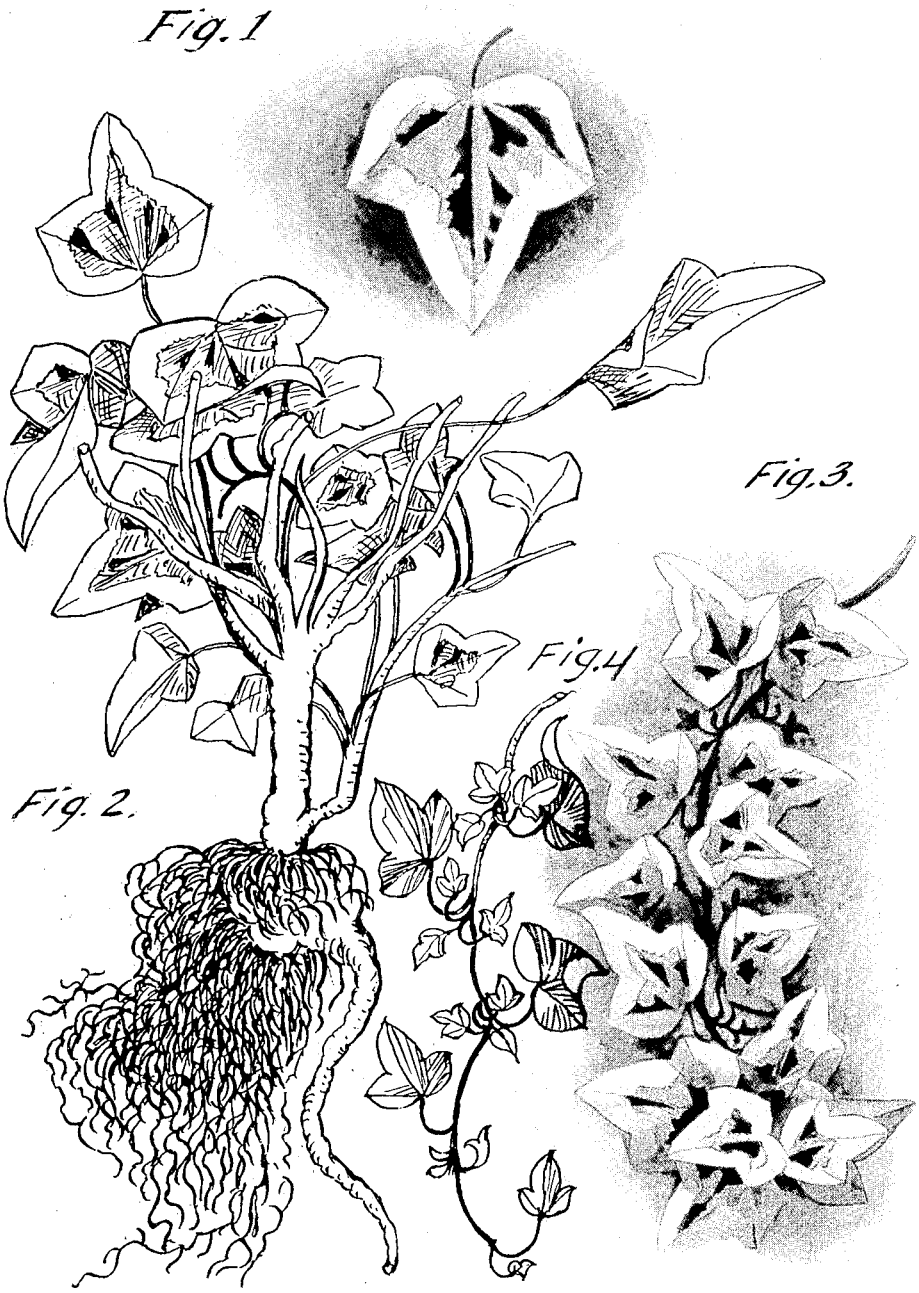
WITNESS
Addison E. Avery
INVENTOR
JOSEPH BACH,
Rummler, Rummler & Snow,
ATTYS.

Patented Sept. 21, 1948

Plant Pat. 807

UNITED STATES PATENT OFFICE

807

IVY PLANT

Joseph Bach, Des Moines, Iowa

Application April 19, 1947, Serial No. 742,665

1 Claim. (Cl. 47—59)

The present discovery relates to a new and distinct variety of ivy plant, which was the result of definite efforts to improve upon the leading commercial ivies. The parent vine was a sport of a branching ivy, which I have asexually propagated by cuttings. The progeny of this new variety have continued to come true to form; thereby perpetuating the novel characteristics.

The unusual features of this new variety reside in its branching tendency and its display of variegated colors in its leaves, which have the usual three pointed lobal form characteristic of ivy plants. The leaf has a distinctive whitish marginal border in a vivid contrast with a grey-green central area containing irregular angular splashes of dark green. These dark green areas spring from and run along the main rib veins of the lobes of the leaf, and their irregular outer edges are defined in tapestry fashion by the threadlike intersecting branch veins.

This new variety is distinctly and outstandingly different from the parent variety especially with respect to its leaf coloring. The leaves are variegated by an attractive array of three contrasting colors, whereas the leaves of the parent plant are of approximately one shade of green throughout. The leaves of my new variety are also smaller in size than the common ivy, being ¾ to 1 inch in width and 1 to 1½ inches in length. To my knowledge this is the only small leaf variegated branching ivy in existence.

To establish these novel and unique characteristics was the primary object of this invention. The new plant grows vigorously and thrives as a house plant, for dish gardens or pot plant.

The accompanying illustration shows in

Figure 1 the characteristic form and coloring of a representative leaf of the new plant.

Fig. 2 is a pen and ink sketch showing how branches spring from the stem, the vines being shown broken off.

Fig. 3 is a view in color of a fragment of vine to show the leaf arrangement thereon; and Fig. 4 is a sketch showing the branching of the vine stems.

Both the nodes and petioles of this new variety are exceptionally short, thus allowing a compactness and bushiness of growth which, combined with the pronounced color scheme, makes this a most attractive and decorative plant. The surface of the leaves is glossy and smooth and the texture leathery. There are three distinct veins in a leaf, which run in a straight line from the base of the leaf to the apex of each lobe. Numerous branched veins spring from these but are inconspicuous except that the contours of the color splashes are defined thereby. This ivy is a vigorous grower and a hardy vine. In its habit of growth and free self-branching quality it is similar to the well-known Hahns Branching Ivy (unpatented).

The color characteristics of my new variety according to Maerz and Paul Dictionary of Color are shown in the following table:

| Section | Plate | Ltr. | No. |
|---|---|---|---|
| Outside border of leaf | 19 | B | 1 |
| Central area of leaf is a Grey-Green | 22 | A | 3 |
| Splashes of dark Green within boundaries of Grey-Green | 24 | H | 9 |

The plant is distinguished by its small-sized leaves, conspicuous coloring, bushy compact growth which affords an abundantly compact mass of foliage.

Figure 4 shows how new branch shoots spring from the vine stems at the base of each leaf petiole. As growth continues, these branches elongate into new vines and develop additional masses of foliage.

Having thus disclosed my invention, I claim:

A new and distinct variety of ivy plant, as herein shown and described, characterized particularly by its compact, branching growth; and by the conspicuous variegated coloring of its leaves, comprising a marginal area of a shade of white surrounding an area of grey-green having a contour of similar shape to that of the leaf and containing angular splashes of dark green.

JOSEPH BACH.